(12) United States Patent
Beam et al.

(10) Patent No.: US 7,061,604 B1
(45) Date of Patent: Jun. 13, 2006

(54) MORTAR PROJECTILE INSPECTION APPARATUS AND METHOD

(75) Inventors: Robert Charles Beam, North Wales, PA (US); John B. Niles, Lake Hopatcong, NJ (US); Drew Diedalis, Oak Ridge, NJ (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 352 days.

(21) Appl. No.: 10/708,148

(22) Filed: Feb. 11, 2004

(51) Int. Cl.
*G01N 21/00* (2006.01)
*G01N 23/00* (2006.01)

(52) U.S. Cl. .................. 356/241.1; 250/390.04
(58) Field of Classification Search .............. None
See application file for complete search history.

(56) References Cited

U.S. PATENT DOCUMENTS

| | | | | |
|---|---|---|---|---|
| 3,733,138 A | * | 5/1973 | Weinberg | 356/241.1 |
| 3,813,174 A | * | 5/1974 | Nowak et al. | 356/241.1 |
| 6,959,108 B1 | * | 10/2005 | Bartelt et al. | 382/141 |

* cited by examiner

*Primary Examiner*—Michael P. Stafira
(74) *Attorney, Agent, or Firm*—Robert Charles Beam; John F. Moran

(57) ABSTRACT

A structural member of a mortar projectile is inspected. The structural member is a composite structure having a thermoplastic matrix with a filler of steel balls. The composite structure has a central cavity into which is placed a strobe light. Surrounding the composite structure is a detection arrangement having a detection medium of photographic film. When the strobe light is activated the film is exposed and developed to obtain an image indicative of the distribution of the steel balls in the matrix. The image is analyzed to determine if the structural member is acceptable.

14 Claims, 6 Drawing Sheets

MORTAR PROJECTILE INSPECTION APPARATUS AND METHOD

FEDERAL RESEARCH STATEMENT

The invention described herein may be manufactured and used by or for the Government of the United States of America for government purposes without the payment of any royalties therefore.

BACKGROUND OF INVENTION

A mortar is an artillery piece having a relatively short smooth bore barrel which fires an explosive projectile in a high arched trajectory. The projectile is fin stabilized and a conventional projectile includes a relatively massive casing containing a propellant and an explosive charge which, upon detonation, causes fragmentation of the casing. In an improved design, the relatively massive casing is replaced by a light weight two-part configuration comprised of a composite structure surrounded by a shell of a light-weight metal such as aluminum.

The composite structure is a two phase structure having a filler of individual members, in the form of metal balls, contained in a matrix of thermoplastic. The composite structure has a longitudinal central cavity into which is placed an explosive charge. The arrangement provides for a greater lethality over the conventional projectile design.

The thin aluminum shell, however, is insufficient to withstand the acceleration forces when the projectile is launched and accordingly, the composite structure forms the structural element of the projectile. Since the metal balls are contained in a relatively weak thermoplastic matrix intended to fragment upon detonation, it is essential that the required amount of balls be placed in the matrix in a relatively homogeneous distribution. At the same time, areas where too many balls are packed tightly together might result in voids in other areas which can lead to structural failure causing the projectile to break apart after launch.

To date there has not been a relatively simple and accurate way to inspect the metal ball/thermoplastic composite structure prior to assembly. The present invention solves the problem.

SUMMARY OF INVENTION

The present invention relates to an apparatus and a method for inspecting a composite structure having a matrix and a filler of individual members subject to uneven distribution in the matrix, with the composite structure having a central longitudinal cavity. The composite structure is placed into a hollow cylindrical detection arrangement and a source of radiation is positioned within the central longitudinal cavity. The source of radiation is operable to project radiation toward the detection arrangement through the composite structure from the central longitudinal cavity. A detection medium carried by the detection arrangement surrounds the composite structure and is responsive to the radiation provided by the source of radiation to obtain an image of the distribution of the individual members in the matrix. The image is analyzed to determine acceptability of the composite structure.

BRIEF DESCRIPTION OF DRAWINGS

The invention will be better understood, and further objects, features and advantages thereof will become more apparent from the following description of the preferred embodiment, taken in conjunction with the accompanying drawings, in which.

DETAILED DESCRIPTION

Figure 1:
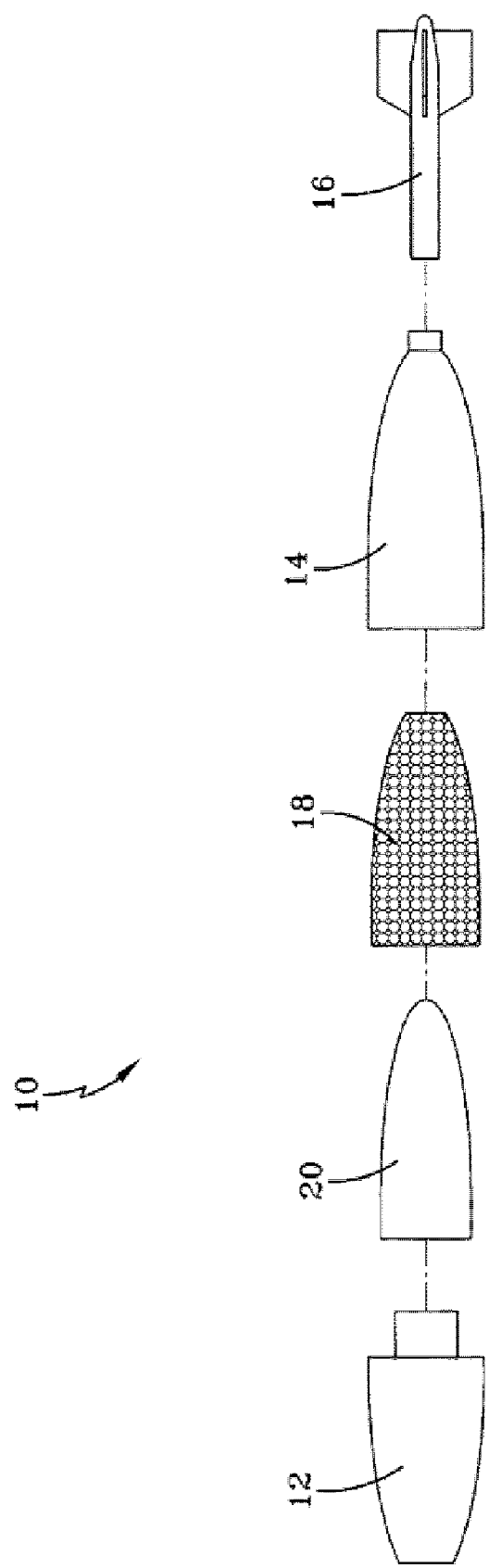
FIG. 1 is an exploded view of a mortar projectile.

In the drawings, which are not necessarily to scale, like or corresponding parts are denoted by like or corresponding reference numerals.

Although the invention is applicable to the inspection of various composite structures, it will be described, by way of example, in conjunction with a mortar projectile of the type illustrated in FIG. 1. In the exploded view of FIG. 1, projectile 10 includes a front end 12, containing a fuze, and, when assembled, is connected to a thin metal body 14, of aluminum, which receives a tail fin assembly 16. Disposed within the body 14 is a conformal composite structure 18 with a central longitudinal cavity into which is placed an explosive charge 20.

Figure 2:
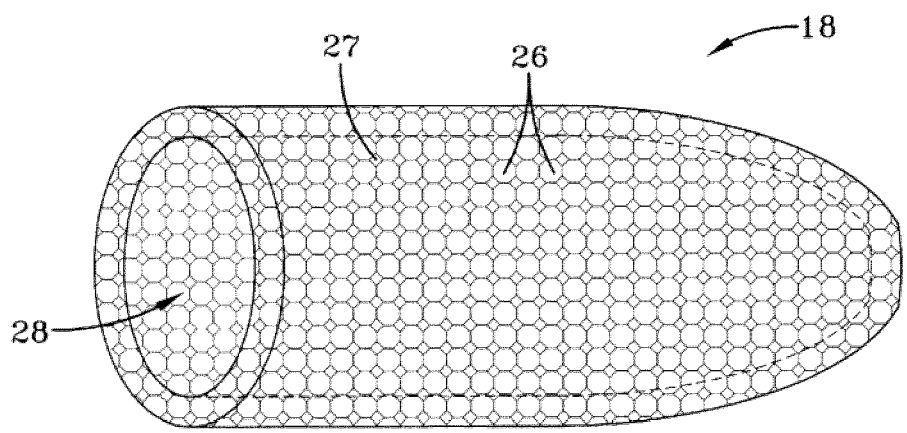
FIG. 2 illustrates a composite structure within the mortar of FIG. 1.

FIG. 2 illustrates the composite structure 18 in more detail. The outside surface of composite structure 18 conforms to the inside surface of the metal body 14 (FIG. 1) and forms the primary structural element of the projectile 10. The composite structure 18 is comprised of a filler of individual members such as metal balls 26, which may of steel, contained in a matrix 27, which may be of a thermoplastic material. These individual members may be of any size or shape, providing they can be packed into the dimension of the composite structure 18. In practice, however, steel balls of uniform diameter slightly less than the wall thickness of the composite structure 18 have been employed advantageously. The composite structure 18 includes a central longitudinal cavity 28, which is used in the inspection process to be described herein, and which subsequently receives the explosive charge of the projectile.

Figure 3:
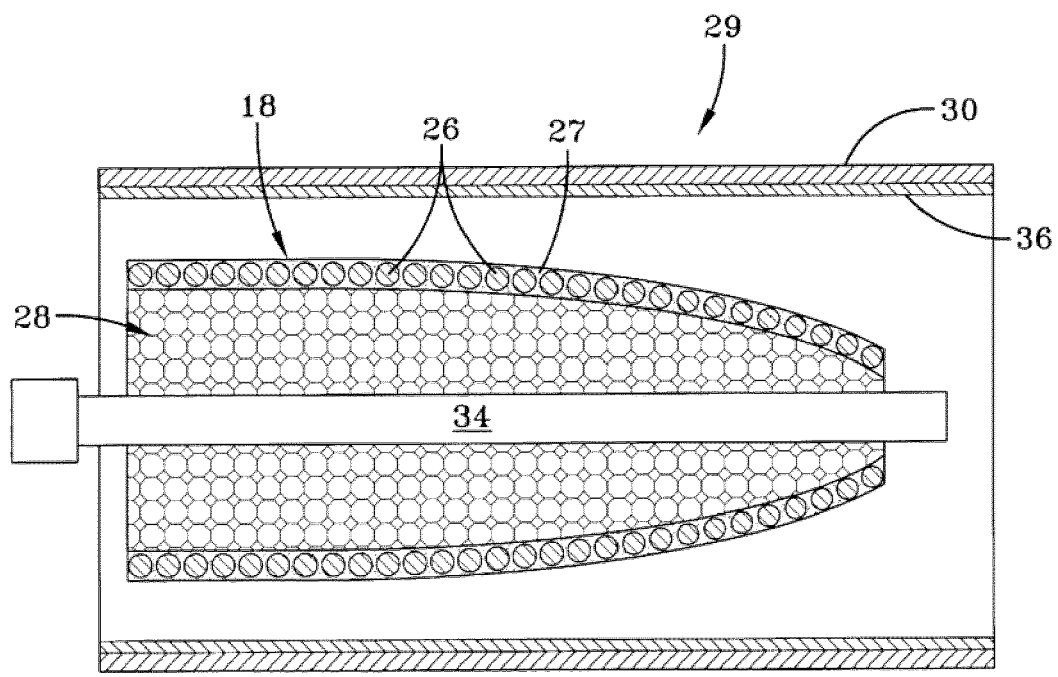
FIG. 3 shows an apparatus for inspecting the structure of FIG. 2.

In FIG. 3, the composite structure 18, shown in cross-section, is positioned within a detection arrangement 29 having a hollow tube 30, also in cross-section. Positioned within the central longitudinal cavity 28 is a source of radiation 34, such as visible light, infrared, ultraviolet or x-rays or any form of electromagnetic radiation. Positioned around the inside surface of hollow tube 30 is a detection medium 36, sensitive to the particular wavelength or wavelengths of the source 34. For example, if source 34 is a strobe light, then detection medium 36 would be photographic film. If the radiation source 34 produces X-rays, then the detection medium would be X-ray film.

Figure 4:
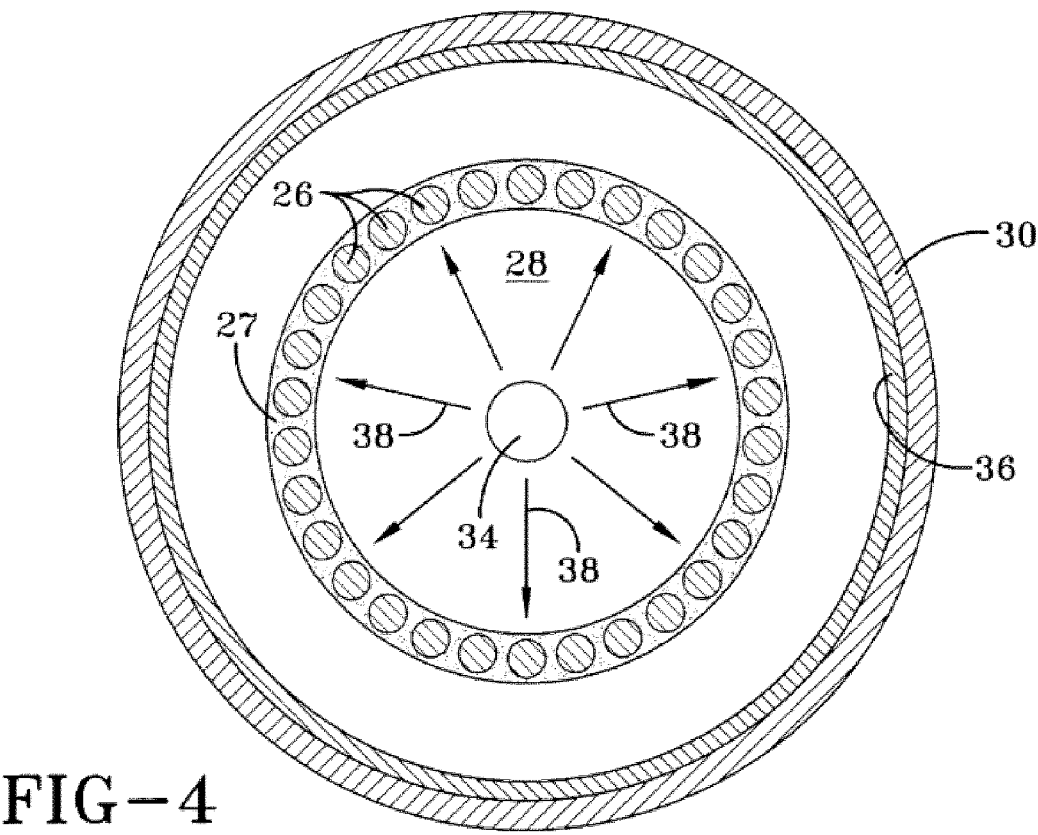
FIG. 4 is a cross-sectional view of the arrangement of FIG. 3.

With additional reference to FIG. 4 which is a radial cross-section (with elements shown in full before sectioning), when strobe light 34 is activated, the visible radiation, as depicted by arrows 38, propagates simultaneously in all radial directions and will be blocked or scattered by steel balls 26 and will be transmitted by thermoplastic matrix 27, which permits transmission of the light to expose film 36. Where there is a uniform distribution of steel balls 26 within the thermoplastic matrix 27 the transmission of radiation would be uniformly scattered resulting in a relatively uniform exposure on the film 36 which would show up as a uniform glow when the film is developed.

Figure 5:
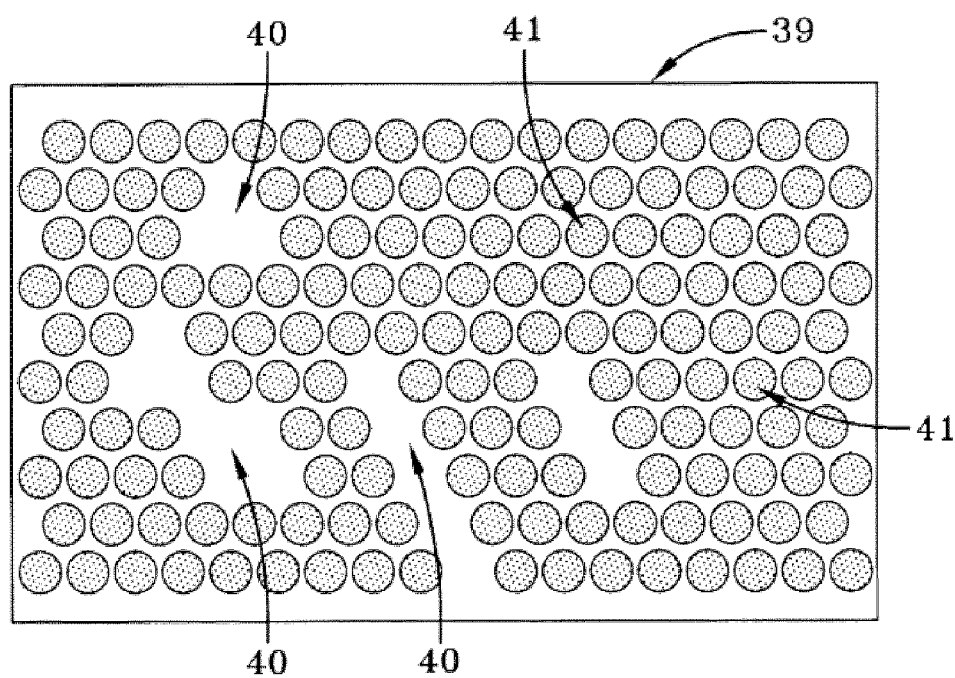
FIG. 5 represents a result of an inspection.

If however, there is an uneven distribution of steel balls 26, this would result in voids appearing in the matrix 27 allowing greater transmission of radiation thereby fully exposing the film 36 in areas where the film is opposite those voids. Where there is a high concentration of steel balls 26, a reduced transmission of radiation would take place and the film 36 would be substantially unexposed. A typical developed film 39 under these conditions is illustrated in FIG. 5 which shows brighter spots 40 where there has been direct transmission of radiation and darker areas 41 where the steel balls are congregated in the matrix.

Figure 6:
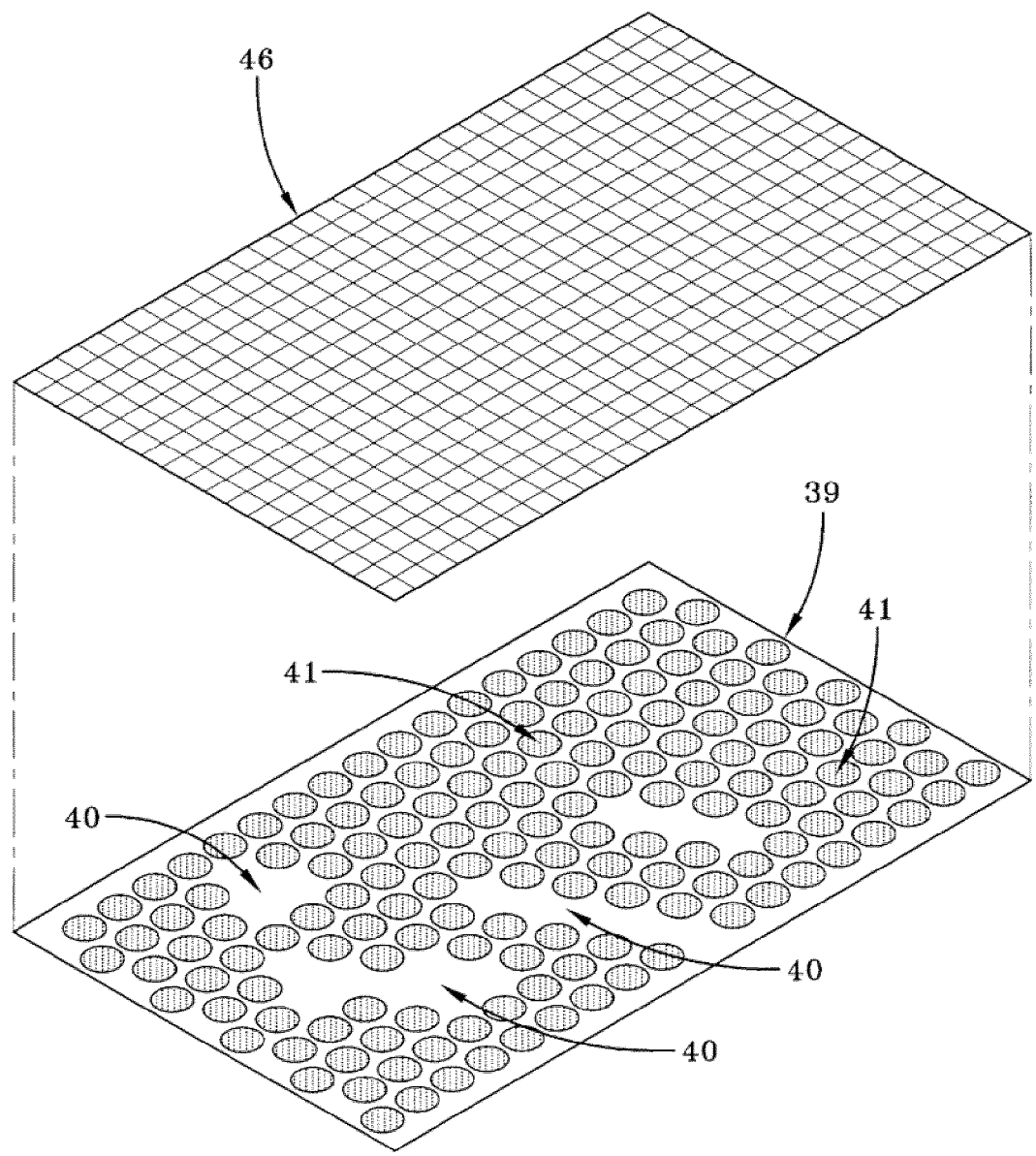
FIG. 6 illustrates one type of analyses which may be used herein.

A simple transparent grid 46, illustrated in FIG. 6, may be placed over the developed film 39 and could provide a quantitative indication of ball distribution. This may be accomplished by counting the resulting white squares and comparing that number with the total number of squares. Such an operation, however, is labor intensive and may only be applicable for relatively small production runs. A more automated arrangement is illustrated in FIG. 7.

After setting up the inspection, as in FIG. 3, the first step in the process, as indicated by block 50 is to activate the radiation source and expose the film surrounding the composite structure 18. Next, the film is developed as indicated by block 52. The developed film 39 is then scanned by a solid state camera 54 to obtain an electronic image of the developed film 39. Such electronic image is then analyzed by an algorithm in computer 56, which will then provide an indication of acceptability of the examined composite structure 18.

Figure 7:
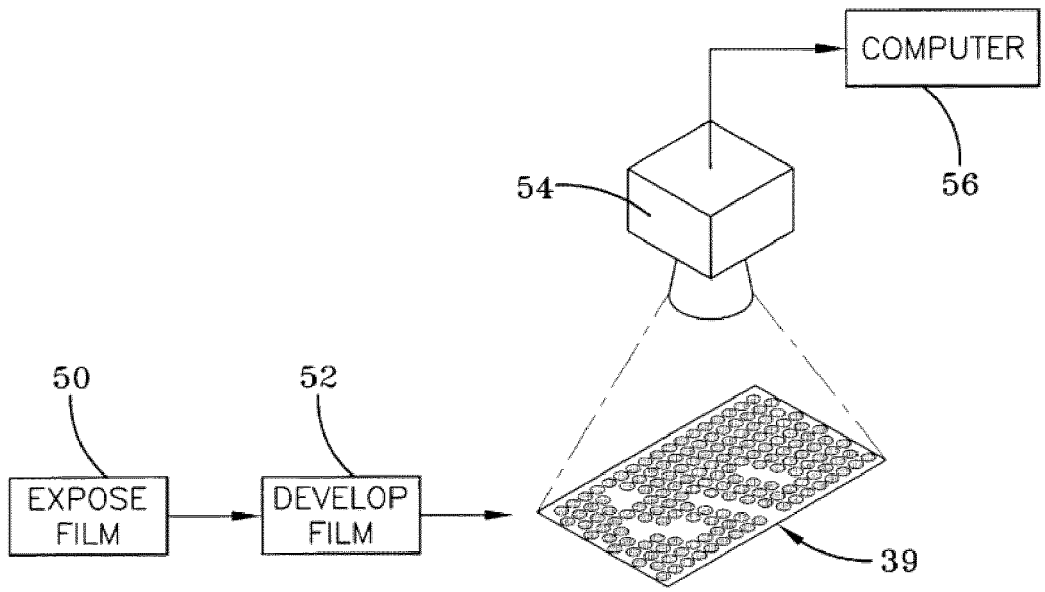
FIG. 7 illustrates another type of analyses which may be used herein.
Figure 8:
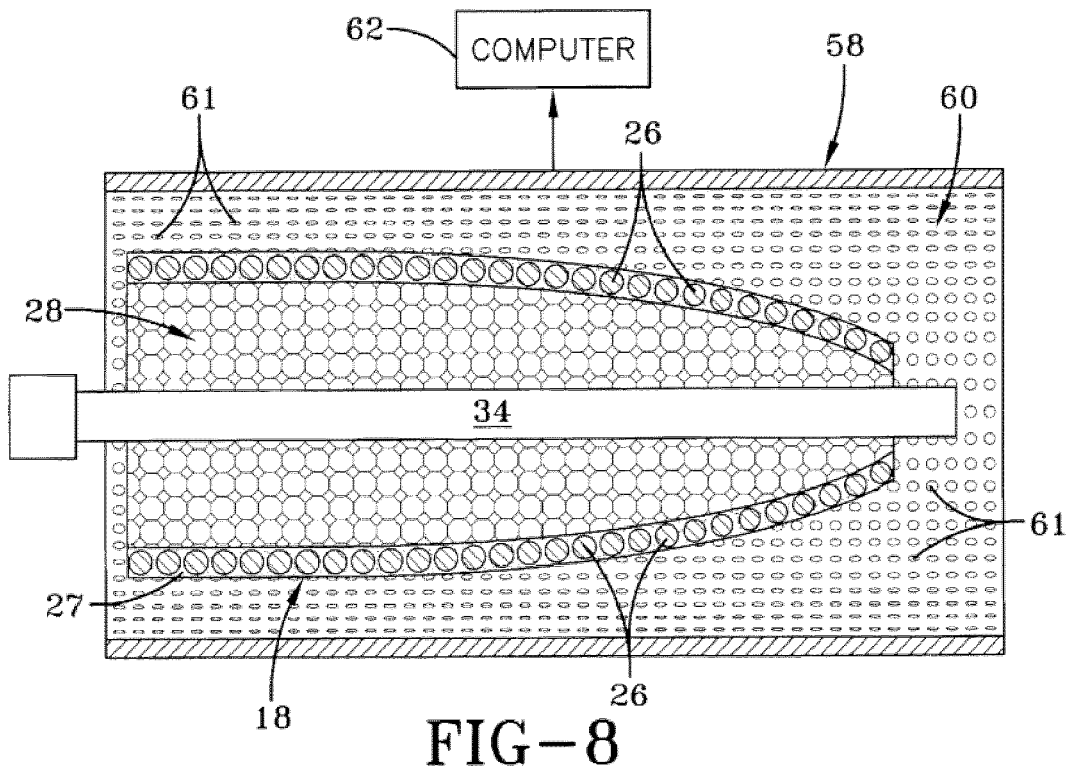
FIG. 8 illustrates another embodiment of the present invention.

Some of the steps of FIG. 7 may be eliminated by the arrangement of FIG. 8, which may be used for large production runs. The detection arrangement 58 is comprised of a cylindrical sensor array 60 having a multitude of individual sensors 61 surrounding the composite structure 18. Each sensor 61 is responsive to the radiation provided by radiation source 34 and will provide an output signal indicative of received radiation. The collective outputs of all the sensors 61 are provided to a computer 62 for analysis, as in FIG. 6.

Figure 9:
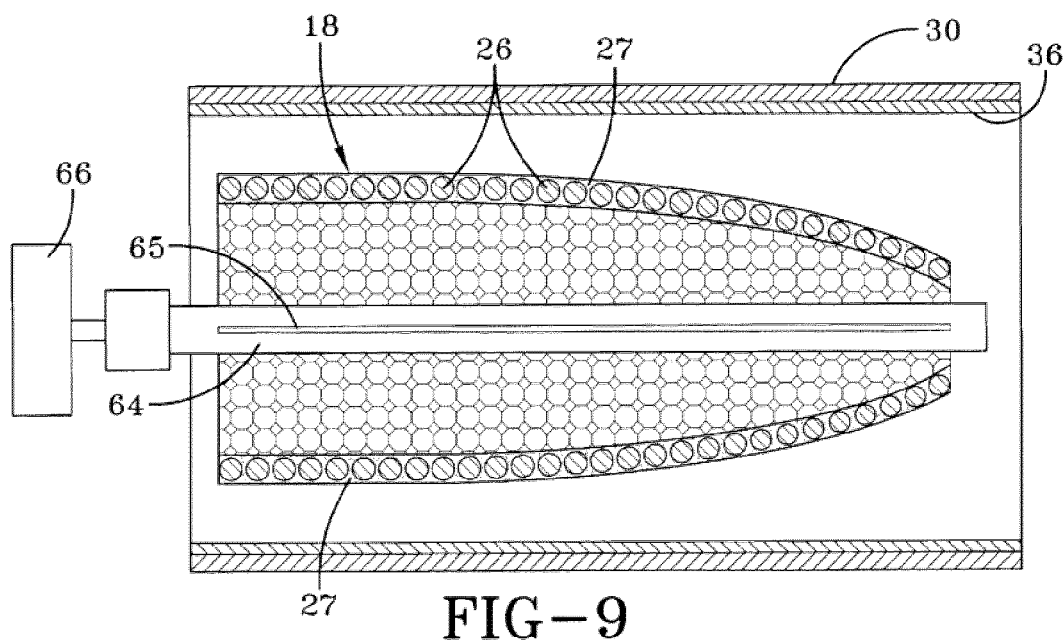
FIG. 9 illustrates yet another embodiment of the present invention.
Figure 10:
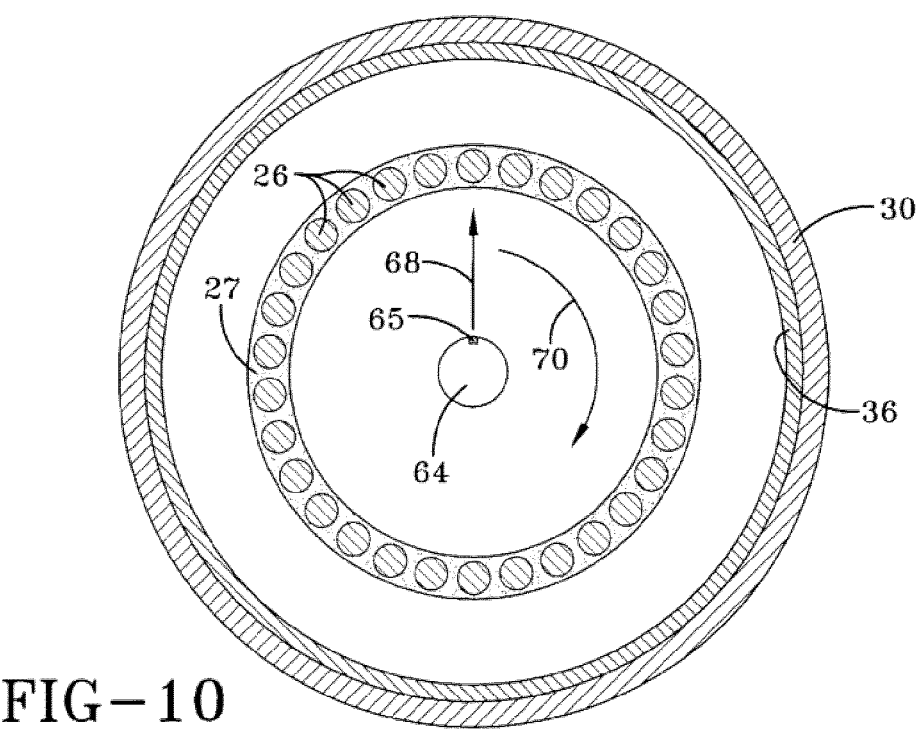
FIG. 10 is a cross-sectional view of the arrangement of FIG. 9.

If a particular source of radiation provides highly directional radiation, as opposed to omnidirectional radiation, as in FIG. 4, then an arrangement such as illustrated in FIG. 9 may be used. Radiation source 64 includes a slit 65 for projection of an elongated narrow beam of radiation. A motor 66 connected to the radiation source 64 rotates it while the radiation beam is being provided, to expose 360 degrees of film 36. The sectional view of FIG. 10 illustrates the source of radiation 64 with radiation beam 68 emerging via slit 65. Rotation of the source of radiation 64 by motor 66 moves the radiation beam 68 in the direction of arrow 70 for a full 360 degree of film exposure.

One skilled in the art would recognize that the exposure of the composite structure 18 to a form of actinic radiation could serve an additional purpose. Many resin materials are photo polymerizable and the actinic radiation might serve as a final curative step, to cross-link a thermoset resin or the like, or to promote micro fracturing which will aid in the uniform fragmentation of the composite structure 18 when an explosive charge is detonated within the structure.

Further, such actinic radiation might cure a surface coating applied to the inside surface of the composite structure 18, such as a coating intended to prevent interaction of the plastic matrix with the explosive fill during storage, or the like.

It will be readily seen by one of ordinary skill in the art that the present invention fulfills all of the objects set forth herein. After reading the foregoing specification, one of ordinary skill in the art will be able to effect various changes, substitutions of equivalents and various other aspects of the present invention as broadly disclosed herein. It is therefore intended that the protection granted hereon be limited only by the definition contained in the appended claims and equivalents. Having thus shown and described what is at present considered to be the preferred embodiment of the present invention, it should be noted that the same has been made by way of illustration and not limitation. Accordingly, all modifications, alterations and changes coming within the spirit and scope of the present invention are herein meant to be included.

What is claimed is:

1. Apparatus for inspecting a composite structure having a matrix and a filler of individual members subject to uneven distribution in the matrix, said composite structure having a central longitudinal cavity, comprising:
    a hollow cylindrical detection arrangement into which said composite structure is placed for inspection;
    a source of radiation positioned within said central longitudinal cavity and operable to project radiation toward said detection arrangement through said composite structure from said central longitudinal cavity;
    a detection medium carried by said detection arrangement and surrounding said composite structure;
    said detection medium being responsive to said radiation provided by said source of radiation to obtain an image of the distribution of said individual members in said matrix.

2. Apparatus according to claim 1 wherein:
    said composite structure is a structural member of a mortar projectile;
    said individual members are steel balls;
    said matrix is a light transmissive thermoplastic;
    said source of radiation is visible light.

3. Apparatus according to claim 1 wherein;
    said detection medium is photographic film.

4. Apparatus according to claim 1 wherein:
    said composite structure is a structural member of a mortar projectile;
    said individual members are metal balls;
    said source of radiation is X-rays.

5. Apparatus according to claim 1 wherein;
    said detection medium is X-ray film.

6. Apparatus according to claim 1 which additionally includes:
    a solid state camera focused on said image of the distribution of said individual members to obtain a corresponding electronic image thereof;
    a computer;
    said electronic image being provided to said computer;
    said computer being operable to analyze said electronic image and provide an indication of said distribution of said members in said matrix.

7. Apparatus according to claim 1 wherein:
    said detection arrangement includes a multitude of individual sensors surrounding said composite structure;

each said sensor being operable to provide a corresponding output signal in response to received radiation projected through said composite structure by said source of radiation; and which includes a computer;

said output signals being provided to said computer;

said computer being operable to analyze said output signals and provide an indication of said distribution of said members in said matrix.

8. Apparatus according to claim 1 wherein:

said source of radiation provides said radiation omnidirectionaly.

9. Apparatus according to claim 8 wherein:

said source of radiation is an elongated strobe light.

10. Apparatus according to claim 1 wherein:

said source of radiation provides a directional beam of radiation; and which includes a motor connected to said source of radiation to rotate it while in said central longitudinal cavity.

11. A method of inspecting a composite structure having a matrix and a filler of individual members subject to uneven distribution in the matrix, and having a central longitudinal cavity, comprising the steps of:

placing said composite structure into a detection arrangement having a detection medium surrounding said composite structure;

placing a source of radiation into said central longitudinal cavity;

activating said source of radiation to project said radiation outward through said composite structure to said detection medium, said detection medium being responsive to said radiation to provide an image of the distribution of said members in said matrix; and analyzing said image.

12. A method according to claim 11 wherein said composite structure is a structural member of a mortar projectile, and said matrix is a light transmissive material, said individual members are metal balls and which includes the steps of:

placing photographic film in said detection arrangement as said detection medium;

placing a strobe light in said central longitudinal cavity as said source of radiation.

13. A method according to claim 11 which includes the steps of:

obtaining an electronic image corresponding to said image of the distribution of said members in said matrix; and providing said electronic image to a computer for said analysis.

14. A method according to claim 11 which includes the steps of:

surrounding said composite structure with an array of sensors, each operable to provide an output signal in response to radiation received from said source of radiation; and providing said output signals to a computer for said analysis.

* * * * *